(12) United States Patent
Neumann

(10) Patent No.: US 9,414,826 B2
(45) Date of Patent: Aug. 16, 2016

(54) RETRACTOR

(75) Inventor: Pavel Neumann, Kullavik (SE)

(73) Assignee: ELOS MEDTECH TIMMERSDALA AB, Timmersdala (SE)

(*) Notice: Subject to any disclaimer, the term of this patent is extended or adjusted under 35 U.S.C. 154(b) by 33 days.

(21) Appl. No.: 13/522,671

(22) PCT Filed: Feb. 9, 2011

(86) PCT No.: PCT/SE2011/050148
§ 371 (c)(1),
(2), (4) Date: Aug. 15, 2012

(87) PCT Pub. No.: WO2011/099928
PCT Pub. Date: Aug. 18, 2011

(65) Prior Publication Data
US 2012/0302838 A1 Nov. 29, 2012

(30) Foreign Application Priority Data
Feb. 12, 2010 (SE) ...................................... 1050145

(51) Int. Cl.
*A61B 1/32* (2006.01)
*A61B 17/02* (2006.01)
*A61B 17/88* (2006.01)

(52) U.S. Cl.
CPC ............. *A61B 17/02* (2013.01); *A61B 17/8866* (2013.01); *A61B 2090/08021* (2016.02)

(58) Field of Classification Search
CPC .... A61B 17/16; A61B 17/1631; A61B 17/02; A61B 17/0206; A61B 2017/0225; A61B 17/0218

USPC ................ 606/90, 99, 96, 104; 600/201–246; 623/201–246, 17.11–17.16
See application file for complete search history.

(56) References Cited

U.S. PATENT DOCUMENTS 4,414,966 A * 11/1983 Stednitz ............. A61B 17/8605
606/308
4,978,350 A * 12/1990 Wagenknecht .... A61B 17/8635
411/387.7

(Continued)

FOREIGN PATENT DOCUMENTS

| CN | 201384559 Y | 1/2010 |
| DE | 824239 C | 12/1951 |

(Continued)

OTHER PUBLICATIONS

Supplementary European Search Report in related European Application No. EP 11 74 2556, dated Sep. 14, 2015.

*Primary Examiner* — Ellen C Hammond
*Assistant Examiner* — Christina Negrellirodrigue
(74) *Attorney, Agent, or Firm* — Knobbe, Martens, Olson & Bear, LLP

(57) ABSTRACT

A surgical retractor comprising an attachment stick, provided with a tip end, intended to be inserted and attached to hard human tissue, such as bone tissue or a vertebra, and at least one shank, attached to the stick, for supporting and keeping organs, muscles and/or tissues at a desired position. The invention is characterized in that said attachment stick has a general shape of a circular cylinder wherein at least one recess is arranged in the outer surface of the stick which recess extends from the tip end in an axial direction of the stick, wherein the recess has a concavely curved shape as seen in a radial cross section taken across the axial direction of the stick.

14 Claims, 2 Drawing Sheets

(56) References Cited

U.S. PATENT DOCUMENTS

| | | | |
|---|---|---|---|
| 6,258,093 B1* | 7/2001 | Edwards et al. | 606/80 |
| 6,699,250 B1 | 3/2004 | Osterle et al. | |
| 7,988,624 B2* | 8/2011 | Smith et al. | 600/210 |
| 2007/0106123 A1 | 5/2007 | Gorek et al. | |
| 2008/0228193 A1* | 9/2008 | Matityahu | 606/99 |
| 2009/0112216 A1* | 4/2009 | Leisinger | A61F 2/4637 606/99 |

FOREIGN PATENT DOCUMENTS

| | | |
|---|---|---|
| WO | WO 01/08564 A1 | 2/2001 |
| WO | WO 2006/003316 A1 | 1/2006 |

* cited by examiner

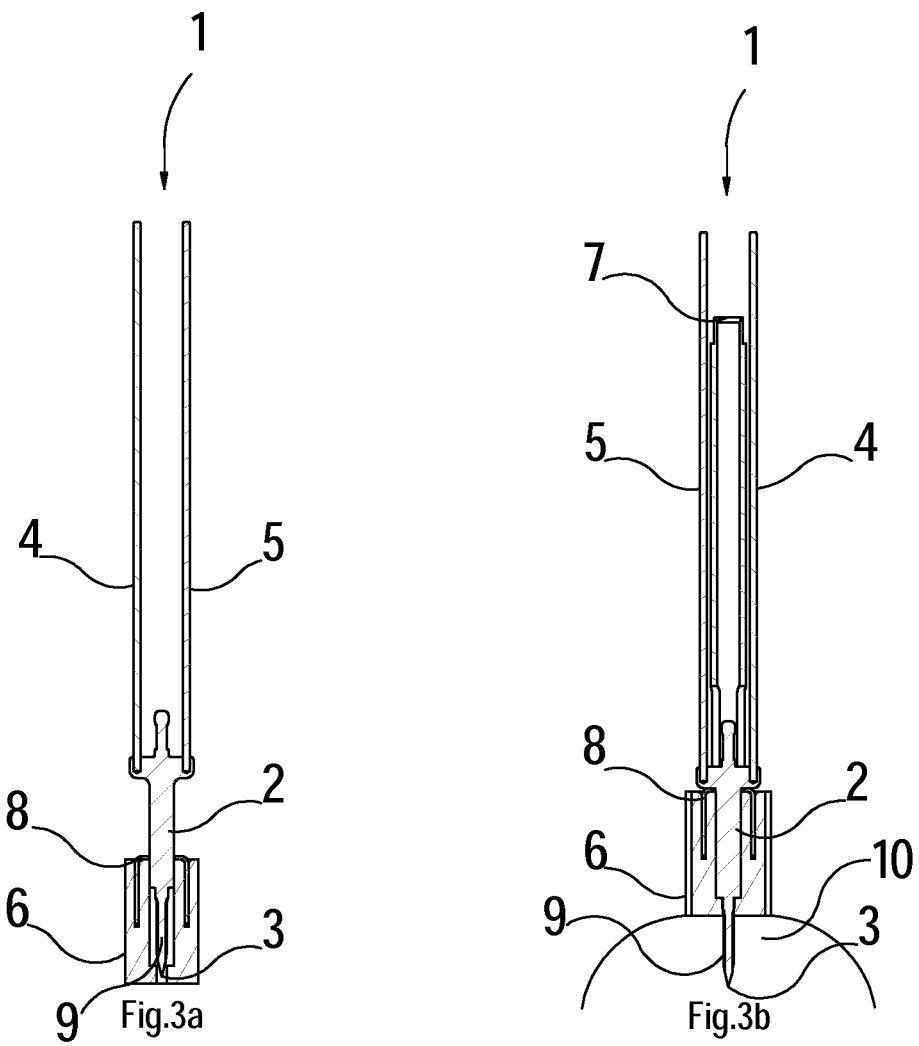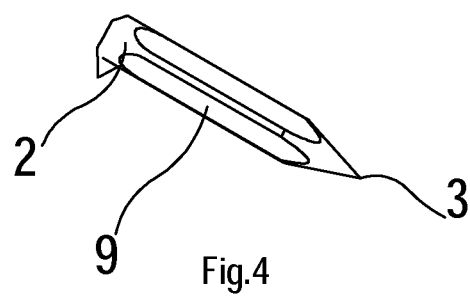

RETRACTOR

TECHNICAL FIELD

The present invention relates to a retractor, i.e. a tool which is used as a holder means for use at e. g. spine surgery. The retractor is intended to be fastened to the patient by for example penetrating one or several sharp pointed pins into a bone structure of the patient, e.g. the spinal column, and having one or several shanks or plates which extends from the pin such that flesh and human tissue may be cautiously relocated and kept away from the spot where the surgeon intends to work and operate on the patient.

BACKGROUND ART

Retractors are known in the art of surgery and may have a variety of different shapes and configurations. A known retractor is for example described in WO 01/08564 wherein the retractor is attached by spiking a sharp pointed end of a pin into the spinal column. The retractor is provided with a cover means covering the pin such that the pin may be spiked into the spinal column while the cover means is protecting tissue from being damaged while the pin is introduced into or taken out of the spinal column. When the retractor is attached to the spinal column the shanks may be bent in order to control how the intestines, human tissue or other soft parts of the patient are kept away from the spot where the surgeon wants to access.

US 2003/149341 describes a retractor arrangement which is preferably attached to the spinal bone by drilling pilot holes into the vertebrate and then screw threaded anchors into the holes. The attachment is thus very rigid but it is a rather complicated system to use in practice.

A further retractor is for example known by JP 2003-169809, where threaded tips of pins are screwed into the bone.

Even though these retractors are functioning, there is a desire for an improved retractor.

DISCLOSURE OF INVENTION

The invention relates to a retractor for surgery use. A retractor is for example used during operations to keep away human tissue from the location of operation such that it facilitates for the person (e.g. a doctor) operating on a patient to more easily access the desired area with his instruments. The retractor comprises an attachment stick intended to be inserted and attached to hard human tissue, e.g. bone tissue or a vertebra. In order to be attached to the hard human tissue, the retractor is provided with a tip end such that the end of the attachment stick may be introduced into the tissue and thus allows the attachment stick to be attached to the hard human tissue. The retractor further comprises at least one shank attached to the attachment stick. In a simple form of a retractor the shank may simply be the extension of the attachment stick protruding from the hard human tissue when the attachment stick is inserted into the hard human tissue. The purpose of the at least one shank is to support, or keep out of the way, organs, muscles and/or tissues such that they do not interfere with the operation performed by the doctor or physician and the tissues are thus kept at a desired position allowing the operational work to be made smoothly.

In the inventive retractor the attachment stick has a general shape of a circular cylinder wherein at least one recess is arranged in the outer surface of the stick which recess extends from the tip end in an axial direction of the stick, wherein the recess has a concavely curved shape as seen in a radial cross section taken across the axial direction of the stick.

Thus, the radial cross section of the stick, at least along a part close to the tip end, exhibits an outer periphery/circumference with a generally circular shape formed by one or several circular arcs that extend in such a way as to coincide with the same imaginary circle, wherein each pair of end parts of the circular arc(s) are connected by a concave segment, i.e. the curved, concave surface of the at least one recess or open hollow.

When such a retractor is inserted in an axial direction into the tissue, the tissue will surround the outer periphery of the stick and thus occupy the space in each of the recesses. This way, free rotation of the stick is prevented when the stick is inserted into and attached to hard human tissue. Since rotation of individual sticks is prevented this has in turn the effect that a lower number of sticks are needed to be attached to a patient to be operated. A lower number of sticks to be attached simplifies the whole process of attaching retractors and it also reduces the risk of bleedings or other problems related to the insertion of sticks into human tissue (since each stick and each hole left by the stick has a certain probability of causing problems).

Further, due to the combination of (convex) circular and concave surfaces arranged side by side the pin can be removed relatively easily and with a reduced risk of causing cracks in e.g. bone tissue. Removal is done by first forcing the stick to rotate and then simply pulling it out in an axial direction. When the retractor according to invention is rotated the circular surfaces (arcs) together with the tip end keep the stick well centered around its center axis while the edges formed where the convex and the concave surfaces meet (i.e. the longitudinal edges of the at least one recess) are capable of cutting a circular hole with a minimum diameter in the tissue. In principal, the sharper the edges, the cleaner the cut.

A stick without such circular arcs, for instance a stick having a polygonal cross section with sharp edges, is not self-centered to the same degree and rather generates compression forces that tend to crush the tissue which might lead to cracks.

The shape of the stick of the inventive retractor, i.e. the general circular shape without sharp parts pointing outwards in a radial direction, also reduces the risk of initiating cracks when the retractor is accidentally bent.

In short, the inventive retractor simplifies attachment and detachment as well as increases the patient safety compared to prior art retractors.

If there are a large number of recesses, e.g. more than 10, the shape approaches that of a circle and the capability of preventing free rotation of the attachment stick will decrease.

The expression "concavely curved" means that the recesses are curved inwards, towards the centre point of the attachment stick, i.e. towards the central, longitudinal axis of the attachment stick.

The shank, or shanks, of the retractor may be made such that its shape may be modified, e.g. by bending of the shanks. If the shanks are made to be bent so as to achieve a desired shape the material should be made of a material which may be plastically bent such that the material maintains its form when reshaped, e.g. metal wires or the like.

The shanks described may of course be used with any of the geometrical configurations of the attachment stick described herein. The use of these bendable shanks, in connection with the described attachment stick, is advantageous since the attachment stick provides an easy and secure attachment of the attachment stick while simultaneously restricting a rotational movement of the stick at its attachment point such that the bent shanks not will deviate from its intended position.

In an embodiment of the invention the number of recesses is at least two, preferably ten or less, more preferably three, four or five. Preferably, the recesses are uniformly distributed around the circumference of the stick.

In an embodiment of the invention each of the circular arcs formed between adjacent recesses at the periphery of the stick has an angle of at least 6°.

In an embodiment of the invention the total angle of the circular arcs formed between adjacent recesses at the periphery of the stick is at least 36°.

In an embodiment of the invention the at least one shank is made of a material that makes the shank capable of being plastically bent such that the shank forms a desired shape.

In an embodiment of the invention the retractor comprises a cover surrounding the attachment stick, wherein the stick is arranged to be axially movable in relation to the cover such that the tip end of the stick is surrounded by the cover in a first, localization mode and the tip end is protruding from the cover in a second, attachment mode.

In an embodiment of the invention said cover comprises a soft material covering a least a part of the outer surface of the cover and a rigid structure preventing compression in the longitudinal direction of the cover when subjected to forces in the longitudinal direction.

BRIEF DESCRIPTION OF DRAWINGS

FIG. 3a A cross sectional view of the retractor in FIG. 1.

FIG. 3b A cross sectional view of the retractor in FIG. 1 attached to human tissue.

FIG. 4 A perspective view of a part of the retractor in FIG. 1.

EMBODIMENTS OF THE INVENTION

Figure 1:
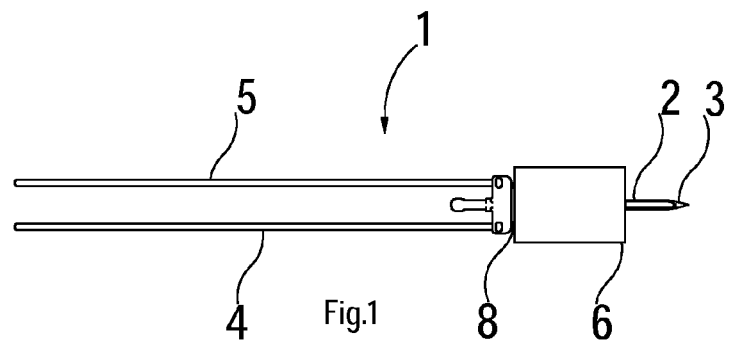
FIG. 1 An overview of a first embodiment of a retractor according to the invention.
Figures 2A, 2B, 2C:
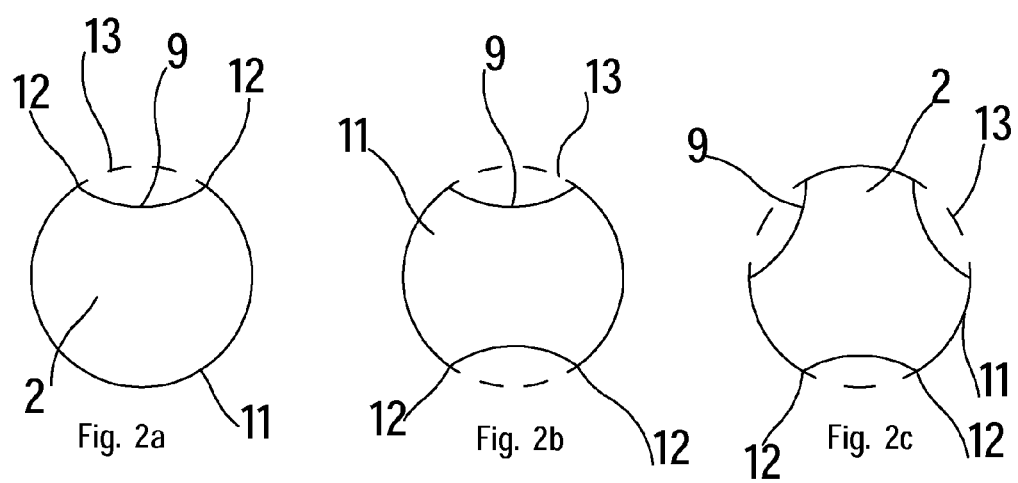
FIG. 2 Cross sectional views of different geometries of the attachment stick of the inventive reactor.
Figures 2D, 2E:
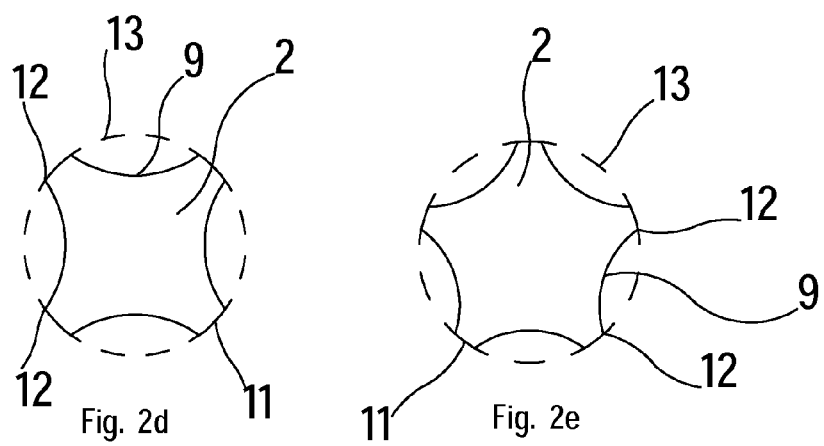

FIG. 1 shows a retractor 1 comprising an attachment stick 2 provided with a tip end 3. The attachment stick 2 is intended to be fastened to human tissue such as bone, vertebra or other hard tissue in the body. The tip end 3 is sharply pointed such as to facilitate attachment to the human tissue, which can be done by beating a back end, or an additional part 7 (see FIG. 3b) placed at the back end, of the attachment stick 2. The retractor further comprises two shanks 4, 5, which are used to relocate and keep away human tissue from undesired locations, and a protection cover 6. A steel insertion 8 is also indicated in FIG. 1.

The attachment stick 2 has, at least along a part close to the tip end 3 intended to be inserted into human tissue, a general shape of a circular cylinder wherein at least one recess 9 (see FIGS. 3a, 3b and 4) is arranged in the outer surface of the stick 2 which recess 9 extends from the tip end 3 in an axial direction of the stick 2. The recess 9 has a concavely curved shape as seen in a radial cross section taken across the axial direction of the stick 2.

FIG. 2a-2e show different examples of radial cross sections (perpendicular to the longitudinal extension of the stick 2) of the attachment stick 2, which cross sections correspond to different designs of the recesses 9 arranged in the outer surface of the stick 2. Thus, each of FIGS. 2a-2e shows a variant of the stick 2 that can be used with the retractor shown in FIG. 1.

As seen in FIGS. 2a-2e, each radial cross section exhibits an outer periphery/circumference with a generally circular shape formed by one or several circular arcs 11 that extend in such a way as to coincide with the same imaginary circle 13, wherein each pair of end parts of the circular arc(s) 11 are connected by a concave segment 9, i.e. the curved, concave surface of the at least one recess 9 or open hollow.

Edges 12 are formed where the convex surfaces of the circular segments 11 meet the concave surfaces/segments 9. These edges 12 thus correspond to the longitudinal edges of the at least one recess 9 arranged in the stick 2.

FIGS. 2a-2e show examples with 1-5 recesses, respectively. In FIGS. 2b-2e the recesses 9 are uniformly distributed along the circumference of the stick 2. A number of recesses 9 within the range 3-5 is likely to be the most advantageous with regard to function and manufacture.

Each of the circular arcs 11 should have an arc length/angle of at least 6° and the total arc length/angle of the circular arcs should be at least 36°. In other words, the circumferential distance (in degrees) between adjacent recesses 9 should be at least 6° and the total circumferential distance occupied by recesses 9 should not be more than 324°.

The curvature of the recesses 9, i.e. the curvature of the concave segments, may be varied depending on the application, and the curvature of a single recess 9 (concave segment) may vary. Also the circumferential length (in relation the imaginary circle 13) of the recesses 9 can be varied.

FIG. 3a shows a cross sectional view of the retractor in FIG. 1 and FIG. 3b shows a cross sectional view of the retractor in FIG. 1 attached to human tissue 10.

The main purpose of the protection cover 6 is to protect the surrounding tissues from sharp edges of the retractor 1. The protection cover 6 is movable relatively the attachment stick 2 in an axial direction such that the tip end 3 of the attachment stick 2 is withdrawn into the cover 6 when the retractor 1 is in its protective (transport) mode. The protective configuration is shown in FIG. 3 a. In a second mode (attachment mode), see FIG. 3b, the tip end 3 and the part of the stick 2 being provided with the recesses 9 protrudes from the cover. The cover 6 may be tubular shaped having the attachment stick 2 positioned in the centre along the longitudinal axis of the cover 6. The cover 6 is particularly useful when attaching the retractor 1 to its attachment point, e.g. by beating/hammering, since the cover 6 protects the surrounding tissues close to the attachment point from friction or shear forces when the attachment stick 2 is inserted into the hard human tissue since the attachment stick not will be in direct contact with surrounding tissues but with the protection cover 6. In order to function as a protection for the tissues while at the same time having a structure preventing the cover from being squeezed when inserted into its attachment site, the cover comprises a soft material covering a least a part of the outer surface of the protection cover and a rigid structure preventing compression in the longitudinal direction of the cover when subjected to forces in the longitudinal direction. The cover may for example comprise a rigid, inner tubular element forming the inner side of the protective cover and being in contact with the attachment stick while the radially outer part of the cover is made of a soft material preventing or decreasing the risk of injuries to human tissues in contact with the cover. The cover may also comprise other load bearing support structures which prevents the compression of the cover in the axial direction due to forces working in the axial direction, e.g. due to spiking when attaching the stick to its attachment point.

FIGS. 3a and 3b show that the cover 6 is provided with a steel insertion 8. The purpose of the insertion 8 is to stiffen the cover 6, to distribute the forces from a tool used to detach the stick 2 and to prevent a too extensive compression of the cover (to avoid that the stick 2 is inserted too long into the tissue). By placing the insertion 8 on the inside of the cover 6 it will not fall off from the cover 6 even if the cover 6 comes off from the retractor 1.

When the retractor 6 shall be attached to a desired location, the retractor is positioned at the location being in its protective configuration such that the risk for damaging any tissue by the tip end is reduced. When the retractor has been located at the desired location, the attachment stick 2 is attached to the tissue by means for example by a hammer. While hitting an intermediate shaft 7, attached to the attachment stick, 2, the tip end 3 will start to protrude from the protective cover 6 and entering into the human tissue 10, see FIG. 3*b*. Hence, the protective cover 6 will protect any neighbouring tissue to be subjected to sheer forces from the attachment stick 2 while hammering the stick into the tissue. The attachment stick 2 is thus introduced into the tissue a desired distance as shown in FIG. 3 *b*. The use of an attachment 2 having such a cross sectional area as exemplified in FIG. 2, preventing rotation of the retractor, will also assure that there will be no rotation, and thus no shear forces on the tissue surrounding the retractor due to any rotational movement during insertion of the tip end 3 into the human tissue.

When the retractor is positioned in the desired position, the shanks 4, 5 may be bent to achieve a desired configuration. Due to the rotational restriction of the retractor 1, the shanks 4, 5 will maintain their position relatively the attachment point and the access to the desired location may thus be ensured.

FIG. 4 shows a perspective view of the tip end 3 and a part of the stick 2 provided with four recesses 9 (of which two can be seen in FIG. 4). The example shown in FIG. 4 corresponds to the cross section shown in FIG. 2*d*.

The generally circular part of the stick 2 provided with recesses 9 may have a slightly varying diameter along its length to simplify insertion and/or removal.

As seen in e.g. FIG. 3*b* It is not necessary that the complete attachment stick 2 exhibits the cross sectional geometries exemplified in FIG. 2*a*-2*e*; it is sufficient that this geometry starts sufficiently close to the tip end 3, so that tissue will occupy the recesses 9 when the stick 2 is inserted, and extends a sufficiently long distance along the stick 2, so that free rotation becomes prevented.

The invention claimed is:

1. A surgical retractor comprising:
    an attachment stick, comprising a circular cylinder portion having a cross-sectional area configured to prevent rotation of the retractor and a taper portion, wherein the taper portion extends from the circular cylinder portion to a sharply pointed tip end sufficiently sharp to be hammered or beaten into hard tissue, wherein at least one recess is arranged in the outer surface of the circular cylinder portion of the stick, which recess extends from a point within the taper portion toward an end opposite the tip end of the stick in a straight line in only a direction parallel to the longitudinal axis of the stick, wherein the recess has a concavely curved shape in a radial cross section taken across the axial direction of the stick, and wherein no part of the taper portion is wider than the stick, and
    at least one shank, attached to the stick, for supporting and keeping organs, muscles and/or tissues at a desired position.

2. A retractor according to claim 1, wherein the number of recesses is at least two.

3. A retractor according to claim 2, wherein the recesses are uniformly distributed around the circumference of the stick.

4. A retractor according to claim 1, wherein the number of recesses is 3, 4 or 5.

5. A retractor according to claim 1, wherein the number of recesses is 10 or less.

6. A retractor according to claim 2, wherein circular arcs formed between adjacent recesses at the periphery of the stick have an angle of at least 6°.

7. A retractor according to claim 2, wherein the total angle of circular arcs formed between adjacent recesses at the periphery of the stick is at least 36°.

8. A retractor according to claim 1, wherein the at least one shank is made of a material that makes the at least one shank capable of being plastically bent such that the at least one shank forms a desired shape.

9. A retractor according to claim 1, wherein the retractor comprises a cover surrounding the attachment stick, wherein the stick is arranged to be axially movable in relation to the cover such that the tip end of the stick is surrounded by the cover in a first, localization mode and the tip end protrudes from the cover in a second, attachment mode.

10. A retractor according to claim 9 wherein said cover comprises a soft material covering a least a part of the outer surface of the cover and a rigid structure preventing compression in the longitudinal direction of the cover when subjected to forces in the longitudinal direction.

11. The retractor of claim 1, wherein the hard tissue is human.

12. The retractor of claim 1, wherein the tip end is configured to be inserted and attached to bone tissue or a vertebra.

13. A method of performing surgery on a subject comprising attaching the retractor of claim 1 to hard tissue.

14. The method of claim 13, wherein the attachment to hard tissue is performed without rotation of the retractor.

* * * * *